United States Patent
Skripko

(10) Patent No.: US 7,507,791 B2
(45) Date of Patent: Mar. 24, 2009

(54) SOLID PHASE PEPTIDE SYNTHESIS OF TRI-PEPTIDE DERIVATIVES

(75) Inventor: Tanja Skripko, Alsbach-Haehnlein (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 152 days.

(21) Appl. No.: 11/244,624

(22) Filed: Oct. 6, 2005

(65) Prior Publication Data

US 2006/0079667 A1  Apr. 13, 2006

(30) Foreign Application Priority Data

Oct. 12, 2004  (EP)  ................................. 04104994

(51) Int. Cl.
*C07K 5/08* (2006.01)
(52) U.S. Cl. ................. 530/331; 530/334; 530/335
(58) Field of Classification Search ................ 530/331, 530/334, 335
See application file for complete search history.

(56) References Cited

U.S. PATENT DOCUMENTS

| 4,070,254 | A | | 1/1978 | Sato et al. |
| 4,428,874 | A | | 1/1984 | Svendsen |
| 4,629,695 | A | | 12/1986 | Svendsen |
| 5,059,525 | A | | 10/1991 | Bartl et al. |
| 5,190,862 | A | | 3/1993 | Wielinger et al. |
| 5,315,035 | A | * | 5/1994 | Frey et al. ..................... 562/16 |
| 2003/0146113 | A1 | | 8/2003 | Unkrig et al. |

FOREIGN PATENT DOCUMENTS

WO   WO 00/50612   8/2000

OTHER PUBLICATIONS

Stewart (Solid Phase Peptide Synthesis, pp. 1-25, Pierce Chemical Company, Rockford, Illinois, 1984).*
Barany (Int. J. Peptide Protein Res. 30, 705-739, 1987).*
Kirby et al, *Biochem*, 18(16) p. 3570-3577, (1979).
Nastri et al, *J. Med. Chem.* 39(10) p. 2008-2017, (1996).
Kobayashi et al, *Arch. Androl.* 27(3) p. 197-206, (1991).

* cited by examiner

*Primary Examiner*—David Lukton
(74) *Attorney, Agent, or Firm*—George W. Johnston; Dennis P. Tramaloni

(57) ABSTRACT

The present invention relates to a process for the preparation of a peptide derivative, and more preferably tri-peptide derivatives, of the formula

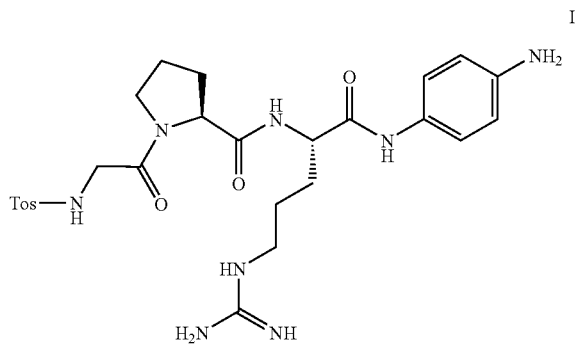

wherein Tos has the meaning of p-toluenesulfonyl.

11 Claims, No Drawings

SOLID PHASE PEPTIDE SYNTHESIS OF TRI-PEPTIDE DERIVATIVES

PRIORITY RELATED APPLICATIONS

This application claims the benefit of European Application No. 04104994.1, filed Oct. 12, 2004, which is hereby incorporated by reference in its entirety.

FIELD OF THE INVENTION

The present invention relates to a process for the preparation of a peptide derivative, and more preferably tri-peptide derivatives, of the formula

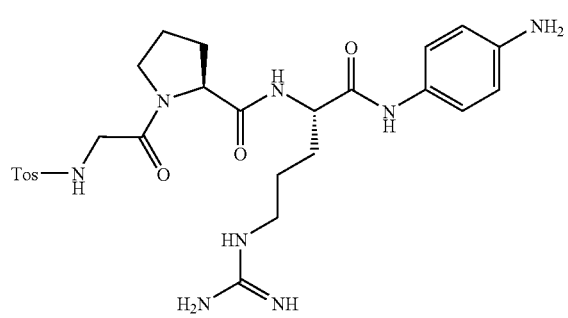

I wherein Tos has the meaning of p-toluenesulfonyl.

BACKGROUND OF THE INVENTION

The peptide derivatives produced according to the present invention are suitable for the quantitative determination of certain proteolytic enzymes of class EC 3.4.4 and especially for thrombin (EC is the abbreviation for "Enzyme Committee" of the International Union of Biochemistry).

Methods for the synthesis of such related peptides have been described e.g. in U.S. Pat. No. 4,428,874 (1984), U.S. Pat. No. 4,070,245 (1978) and U.S. Pat. No. 4,629,695 (1986). These methods are based on solution phase synthesis using different amino acid derivatives.

However, the methods described in the art are not satisfactory with regard to the optical purity of the desired isomer and regarding the efforts needed for the purification of the respective peptides.

Accordingly, the object of the present invention therefore is to provide a more economic process for the manufacture of the peptide derivative of formula 1 in good yield and high optical purity.

The object has been achieved with the process of the present invention according to the claims herein.

SUMMARY OF THE INVENTION

The present invention relates to a process for the preparation of a peptide derivative, and more preferably tri-peptide derivatives, of the formula I

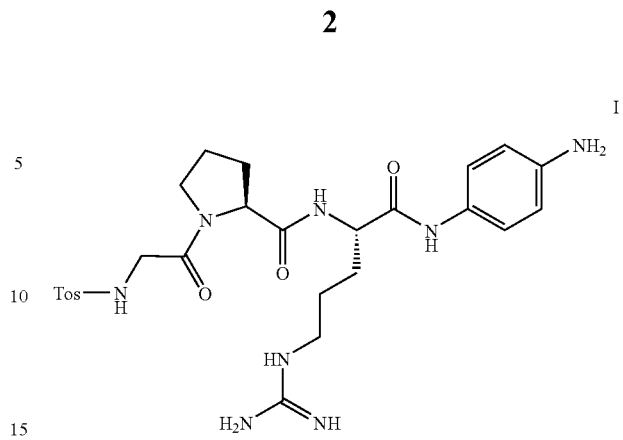

I wherein Tos has the meaning of p-toluenesulfonyl.

The process of the present invention is based on solid phase synthesis. During solid phase synthesis, amino acids are assembled (i.e., coupled) into a peptide of any desired sequence while the starting material is bonded to an inert solid support. Reactants are added in solution, because the starting product is bonded to the solid, any product from the starting material remains bonded as well. Once the desired sequence has been linked together on the support, the peptide is detached (i.e., cleaved) from the support.

The process comprises a) consecutive coupling of the amino acids arginine, proline and glycine on a solid phase support in the presence of a first coupling agent/additive system.

b) tosylation of the N-α-amino group of the glycine moiety, c) cleavage of the tosylated peptide or of an amino side chain protected derivative thereof from the solid phase support to form the peptide intermediate of formula II

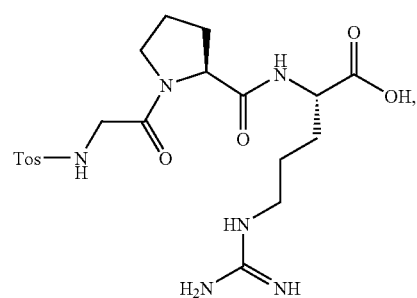

II or an amino side chain protective derivative thereof; and d) reaction, in the presence of a second coupling agent/additive system, of the peptide intermediate of the formula II

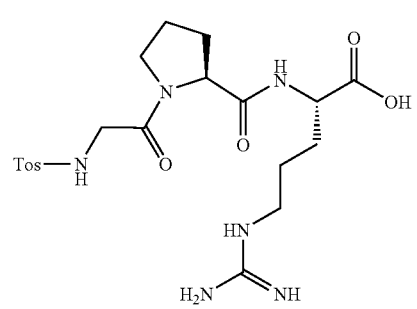

II or of an amino side chain protected derivative thereof with an aniline of the formula III

   III wherein R has the meaning of p-aminophenyl and wherein one amino group is protected with an amino protecting group.

DETAILED DESCRIPTION OF THE INVENTION

The present invention relates to a process for the preparation of a peptide derivative, and more preferably tri-peptide derivatives, of the formula I

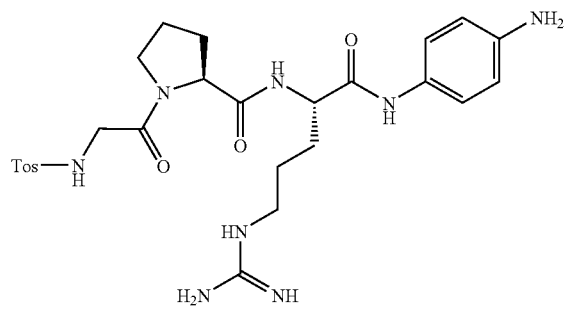

wherein Tos has the meaning of p-toluenesulfonyl.

The meaning of the abbreviations used in the description and the claims is as outlined in the table below:

| | |
|---|---|
| Fmoc | 9-Fluorenylmethoxycarbonyl- |
| Boc | t-Butoxycarbonyl- |
| Tos | 4-Toluenesulfonyl- |
| DIEA | Diisopropylethylamine |
| NMP | N-Methylpyrrolidon |
| DCM | Dichloromethane |
| TFA | Trifluoraceticacid |
| DMF | N,N'-Dimethylformamide |
| HBTU | O-Benzotriazole N,N,N',N'-tetramthyl-uronium-hexafluoro-phosphate |
| HOBt | 1-Hydroxybenzotriazole |
| HOOBt | 3,4-Dihydro-3-hydroxy-4-oxo-1,2,3-benzotriazine |
| DEPBT | 3-(Diethoxyphosphoryloxy)-1,2,3-benzotriazin-4(3H)-one |
| PyBOP | (Benzotriazol-1-yloxy)tripyrrolidinophosphonium hexafluorophosphate |
| CTC | 2-Chlortritylchloride |
| DCC | N,N'-Dicyclohexylcarbodiimide |
| TBTU | O-(Benzotriazol-1-yl)-N,N,N',N'-tetramethyluronium tetrafluoroborate |
| HOAt | 1-Hydroxy-7-azabenzotriazole |
| Pbf | 5-Sulfonyl-2,2,4,6,7-pentamethylbenzofuran |
| Pmc | 6-Sulfonyl-2,2,5,7,8-pentamethylchroman |
| $Et_3N$ | Triethylamine |
| DBU | 1,8-Diazabicyclo[5.4.0]undec-7-ene |
| HATU | O-(7-Azabenzotriazol-1-yl)-N,N,N',N'-tetramethyluronium-hexafluoro-phosphate |

It is further understood that the amino acids arginine and proline can be used either in there L- or in their D-configuration, as racemate or in various mixtures of their isomers. Preferably the amino acids are used in their L-configuration.

The consecutive coupling in step a) of the present invention comprises in a first step the attachment of a preferably protected arginine to a solid phase support.

The α-amino group of arginine can be protected by a common amino protecting group known to the skilled in the art. Fmoc is the preferred α-amino protecting group of arginine.

The side chain i.e. the guanidine part of the arginine molecule as a rule is protected with an arginine side chain protecting group known to the skilled in the art. Preferred arginine side chain protecting group is Pmc or Pbf, more preferred Pbf.

In principle every solid phase support which is known to be useful for solid phase peptide synthesis can be used for the synthesis of the present invention as described in Peptides: Chemistry and Biology, N. Sewald, H.-D. Jakubke, Wiley-V C H Verlag GmbH, Weinheim, 2002 and Fmoc-Solid Phase Peptide Synthesis-A practical approach, W. C. Chan, P. D. White, Oxford University Press Inc. New York, 2000.

It was found that the 2-chlorotritylchloride-polystyrene resins (CTC-resins) are most suitable as solid phase support for the purpose of the peptide synthesis of the present invention. CTC resins are commercially available for example from Merck Bioscience.

The protected arginine is preferably dissolved in an inert solvent such as e.g. in dichloromethane.

A tertiary amine such as $Et_3N$, DIEA or sym-collidine, preferably DIEA or sym-collidine is usually present.

The attachment to the solid phase support as a rule happens at a temperature range of about 10° C. to about 38° C. and more preferably at room temperature (i.e. about 25° C. to about 30° C.).

Work up of the loaded resin follows techniques known to the skilled in the art and includes washing of the resin with organic solvents, filtering and finally drying at modest temperatures.

In a preferred embodiment of this first step Fmoc-Arg (Pbf)-OH loaded CTC-resin is prepared.

In the subsequent steps coupling with the protected proline followed by the coupling with the protected glycine is accomplished.

Before the coupling can take place the α-amino group of arginine has to be deprotected expediently by means of a secondary amine such as morpholine, DBU or piperidine preferably with piperidine in a 5-20% solution with a suitable solvent such as DMF or NMP, preferably with NMP.

The α-amino groups of both proline and of glycine can be protected by common amino protecting group known to the skilled in the art. Fmoc is the preferred α-amino protecting group for both proline and glycine.

Proline may be applied in the form of an activated derivative selected from PG-Pro-OPfp, PG-Pro-OSu and PG-Pro-OBt, or as unactivated derivative in the form of PG-Pro-OH, wherein PG has the meaning of an amino protecting group. Preferably proline is applied in the form of Fmoc-(L)-Pro-OH.

Glycine may be applied in the form of an activated derivative in the form of PG-Gly-OPfp and PG-Gly-OSu or as unactivated derivative in the form of PG-Gly-OH, wherein PG has the meaning of an amino protecting group. Preferably glycine is applied in the form of Fmoc-Gly-OH.

According to the present invention the coupling of amino acids is effected with a first coupling agent/additive system selected from DCC/HOBt; HBTU/HOBt, TBTU/HOBt, HATU/HOAt, DEPBT/HOOBt, PyBoP/Cl-HOBt. A preferred first coupling agent/additive system is DEPBT/HOOBt or HBTU/HOBt, whereby HBTU/HOBt is the most preferred.

Each coupling is commonly performed in the presence of a tertiary amine such as $Et_3N$, DIEA or sym-collidine preferably in DIEA or sym-collidine in a suitable solvent such as NMP.

The coupling reaction ideally takes place at a temperature from 0° C. to 40° C. under stirring.

The deprotection of the proline before coupling with the glycine and finally deprotection of the glycine can be effected expediently by means of a secondary amine such as morpholine, DBU or piperidine, preferably with piperidine in a 5-20% solution with a suitable solvent such as DMF or NMP, preferably with NMP. In a preferred embodiment of this coupling reactions H₂N-Gly-(L)-Pro-(D/L) Arg-(Pbf)-OH loaded CTC-resin is prepared.

Tosylation of the N-α-amino group of the glycine moiety following step b) of the process of the present invention is usually performed with 4-toluenesulfonylchloride in the presence of a tertiary amine such as Et₃N, DIEA or sym-collidine preferably in DIEA. The tosylation as a rule accomplished in the presence of an inert solvent such as dichloromethane at a temperature from 0° C. to 40° C.

The step c) cleavage from the solid phase support can be accomplished by methods known to one of ordinary skill in the art to form the tosylated peptide derivative (peptide intermediate) of formula II

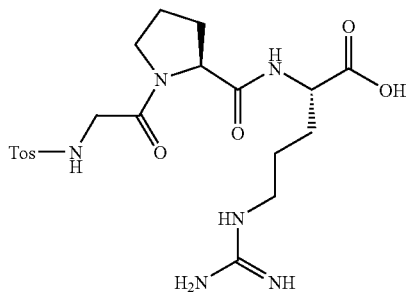

or an amino side chain protected derivative thereof.

Preferably in step c, the desired and preferred peptide derivative (intermediate) Tos-Gly-(L)-Pro-(L)-Arg(Pbf)-OH is cleaved off from the CTC-resin by treatment with a diluted acidic solution preferably with a 0.1-5% solution of trifluoroacetic acid in dichloromethane.

The peptide so obtained may be further purified with methods known in the art, preferably by liquid phase chromatography purification techniques.

According to step d) the tosylated peptide derivative (peptide intermediate of formula II) is coupled with an aniline of formula III

wherein R has the meaning of p-aminophenyl wherein one amino group is protected with an α-amino protecting group, in the presence of a second coupling agent/additive system.

The reaction of step d) (the coupling of the peptide intermediate of formula II with an aniline of formula III) is effected in the presence of a second coupling agent/additive system selected of DCC/HOBt, HBTU/HOBt, TBTU/HOBt, HATU/HOAt, PyBOP/Cl-HOBt, DEPBT/HOOBt, preferably with DEPBT/HOOBt, in the presence of a tertiary amine such as Et₃N, DIEA or sym-collidine, preferably in DIEA. The second coupling agent/additive system (step d) may or may not be the same system as that utilized and selected for the first coupling agent/additive system (step a) of the process of the invention.

The reaction is preferably performed in a suitable solvent such as DMF at a temperature in a range of 0° C. to 40° C. under stirring.

Work up of the reaction mixture follows common knowledge of one of ordinary skill in the art and may involve extraction with a diluted acid such as diluted HCl.

The peptide so obtained may be further purified with methods known in the art, preferably by liquid phase chromatography purification techniques.

With the process of the present inventions the desired peptide isomer could be obtained in excellent yields of up to 85% and with an optical purity of up to 96%.

Another embodiment of the invention encompasses pharmaceutically acceptable salts of the peptide derivatives of formula I. Such salts may be obtained from the peptide derivatives of formula I by procedures known to one of ordinary skill in the art.

The term "pharmaceutically acceptable salts" comprises inorganic acids, e.g., with hydrohalic acids such as hydrochloric acid and hydrobromic acid, sulphuric acid, nitric acid and phosphoric acid, and the like, and with organic acids, e.g. with acetic acid, tartaric acid, succinic acid, fumaric acid, maleic acid, malic acid, salicyclic acid, citric acid, methanesulphonic acid and p-toluene sulphonic acid, and the like. The formulation and isolation of such salts can be carried out according to methods known in the art.

The peptide derivative(s) of the present invention may also be utilized for the quantitative determination of proteolytic enzymes and more particularly the quantitative measurement of thrombin in capillary blood. Exemplary embodiments of such quantitative determination and quantitative measurement in which the peptide derivative(s) of the present invention may be utilized are described in published application US 2003/0146113 which is hereby incorporated by reference in its entirety.

EXAMPLE 1

Attachment of Fmoc-(L)-Arg(Pbf)-OH to CTC-resin 500 g (0.77 mol) Fmoc-(L)-Arg(Pbf) (Merck Biosciences Novobiochem) were dissolved in a stirred solution of 5.5 l dichloromethane and 812 ml (4.77 mol) DIEA. 1 kg CTC-resin (Merck Biosciences GmbH, 100-200 mesh, 1% DVB, loading: 0, 8-1, 6 mmol/g resin) was added and the solution was stirred for approx. 2 min. The mixture was left standing at room temperature for 3 h, whereas after 1 h respectively after 2 h the mixture was stirred for 2 min. After 3 h the mixture was cooled to 5-10° C. and 300 ml methanol were added. The suspension was left to stand for 1 h at this temperature. Then the mixture was filtered on a suction filter.

Then the resin was suspended in a solution of dichloromethane/methanol/DIEA (80:15:5), stirred for 5 min and was left to stand for 30 min. After filtration the resin was washed four times with 5 l DMF, 4 times with 2.5 l isopropanol and three times with 2.5 l isohexane. The resin must be filtrated, that the resin remains wet. Then the resin was dried in a vacuum drying cabinet for 40 h at 30° C.

Loading analysis with HPLC: 0,405 mmol/g Fmoc-Arg (Pbf)-CTC

HPLC method: Column: Keystone Beta Basic C18; mobile phase A: $H_2O+0,1\%$ TFA, mobile phase B: acetonitrile+0,075% TFA, T=30° C., t=22 min, Rt=12.2 min.

EXAMPLE 2

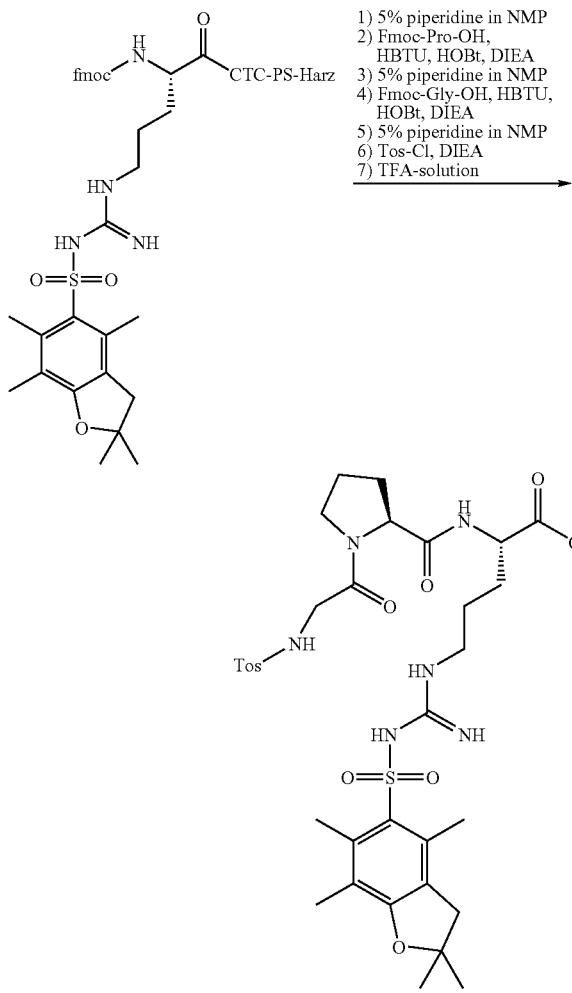

1) 5% piperidine in NMP
2) Fmoc-Pro-OH, HBTU, HOBt, DIEA
3) 5% piperidine in NMP
4) Fmoc-Gly-OH, HBTU, HOBt, DIEA
5) 5% piperidine in NMP
6) Tos-Cl, DIEA
7) TFA-solution A peptide reaction vessel was charged with 5 g Fmoc-(L)-Arg(Pbf)-CTC-resin (loading: 0.405 mmol/g; 2.075 mmol). 87.5 ml dichloromethane has been added. When the resin has been swollen in dichloromethane for at least 30 min, the solvent has been changed to NMP. Thus, washing of the resin with 87.5 ml NMP (3 times) has been accomplished. Deblocking was performed in a solution of 5% piperidine in NMP within 30 min. Subsequently the resin has been washed 6 times with 62.5 ml NMP.

The coupling procedure was performed by preparing a solution of 1.05 g (3.11 mmol) Fmoc-(L)-Pro-OH, 0.477 g (3.11 mmol) HOBt and 1.09 ml (6.22 mmol) DIEA in 8.75 ml NMP and adding of 1.18 g (3.11 mmol) HBTU in 7.5 ml NMP after 5 min. After 10 min preactivation the described solution has been added to the resin and the suspension was carefully stirred for 2 h at 30° C. The coupling was followed by an extensive washing with NMP.

Deblocking of the amino group was performed in a solution of 5% piperidine in NMP within 30 min. Subsequently the resin has been washed extensively with NMP. The coupling procedure was performed by preparing a solution of 0.925 g (3.11 mmol) Fmoc-Gly-OH. 0.477 g (3.11 mmol) HOBt and 1.09 ml (6.22 mmol) 7.5 ml NMP after 5 min. After 10 min. preactivation the described solution has been added to the resin and the suspension was carefully stirred for 2 h at 30° C. The coupling was followed by an extensive washing with NMP.

A last deblocking of the amino group was again performed in a solution of 5% piperidine in NMP within 30 min, followed by an extensive washing with NMP and with dichloromethane (3 times). Then the resin has been suspended in 75 ml dichloromethane and 0.475 g (2.49 mmol) 4-toluenesulfonylchloride (Tos-Cl) and 0.43 ml (2,49 mmol) DIEA has been added. Final cleavage of the peptide was performed with 1% TFA solution in DCM. The filtrate was diluted with toluene and evaporated in vacuum.

1, 7 g of crude peptide (Tos-Gly-(L)-Pro-(L)-Arg (Pbf)-OH) has been obtained.

HPLC: Column: Keystone Beta Basic C18; mobile phase A: $H_2O+0,1\%$ TFA, mobile phase B: acetonitrile+0,1% TFA), T=30° C., t=34 min, Rt=13,9 min, A %: 89,6%, NMR: $^1H$, $^{13}C$ corresponds ESI-MS: $MH^+$ 735.3, $MNa^+$ 757.3; $[M-H]$–733.3

EXAMPLE 3

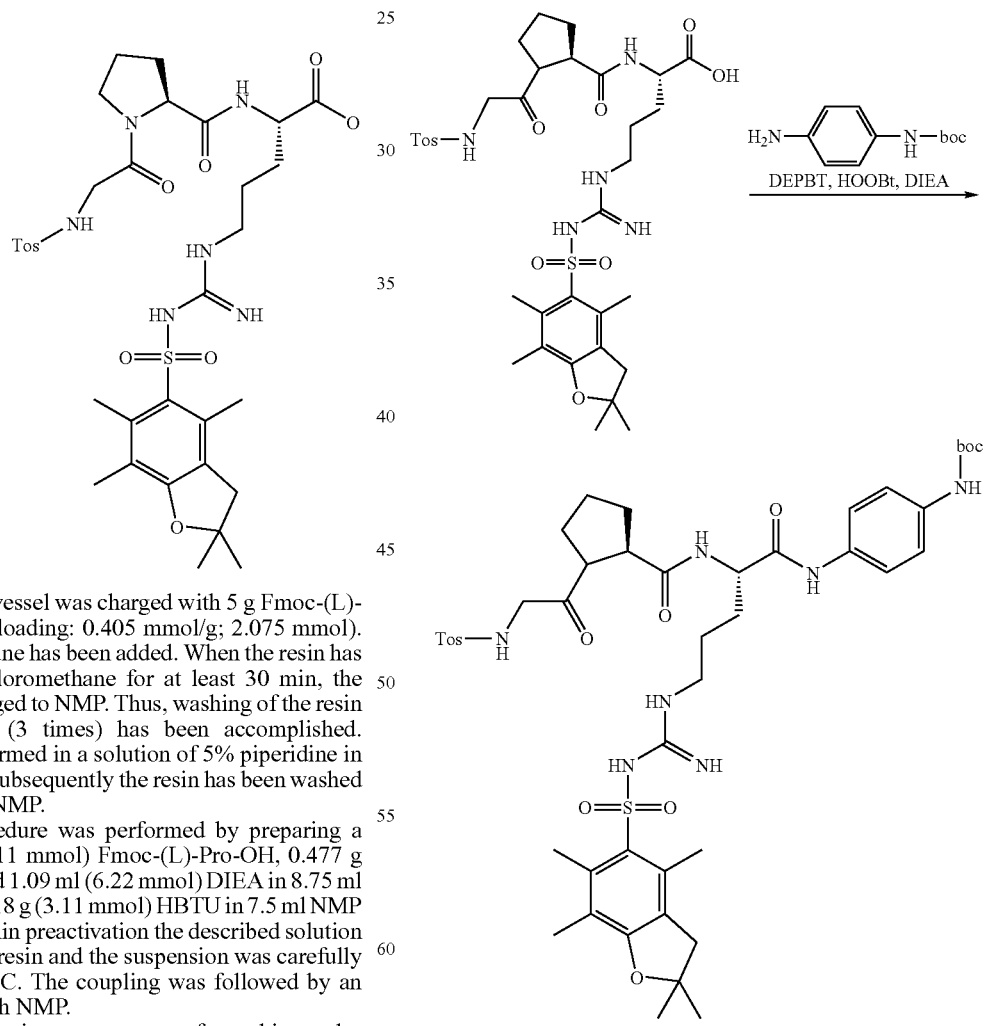

A reaction vessel was charged with 0.61 g (0.83 mmol) Tos-Gly-(L)-Pro-(L)-Arg(Pbf)-OH in 9 ml DMF and 0.135 g (0.83 mmol) HOOBt and 0.29 ml (1.66 mmol) DIEA are added. The preactivation mixture was stirred for five minutes, then 0.248 g (0.83 mmol) DEPBT and 0.156 g (0.75 mmol) N-Boc-p-phenylenediamine were added. After 5 h stirring at room temperature the solvent had been distilled under vacuum. The residue was extracted with aqueous HCl-solution. After chromatographic purification with silica 0.39 g (85%) product has been obtained.

HPLC, method 1: Column: Keystone Beta Basic C18; 150×4,6 mm; gradient method mobile phase A: $H_2O$+0,1% TFA, mobile phase B: acetonitrile+0,1% TFA, T=30° C., t=34 min, Rt=16,11 min, A %: 91,13%, HPLC, method 2: Column: Chirobiotic T; 10 m, 250×4,6 mm; isocratic method mobile phase: ((acetonitrile: MeOH; 1:4)+0,2% $Et_3N$+0,2% AcOH), T=30° C., t=30 min, Rt=4,53 min, A %: 95,4%, NMR: $^1H$ and $^{13}C$: corresponds ESI-MS: $MH^+$ 925.2, $MNa^+$ 947.2, [M-H]−923.2

The above examples and references are provided to aid the understanding of the present invention, the true scope of which is set forth in the appended claims. It is understood that modifications can be made in the procedures set forth without departing from the spirit and scope of the invention.

I claim:

1. A process for the preparation of a peptide derivative or a pharmaceutically acceptable salt thereof of formula I

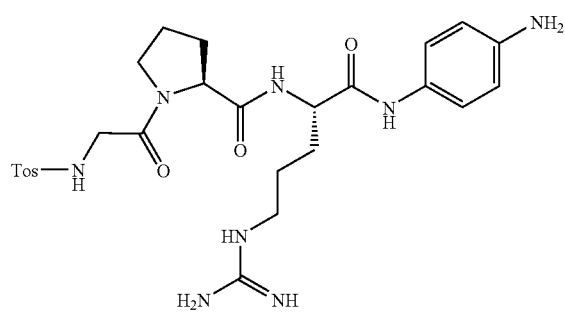

I wherein Tos has the meaning of p-toluenesulfonyl, comprising a) consecutive coupling of the amino acids arginine, proline and glycine on a solid phase support in the presence of a first coupling agent/additive system, wherein the solid phase support is a 2-chlorotritylchloride-polystyrene resin and wherein further the first coupling agent/additive system is selected from the group consisting of DCC/HOBt, HBTU/HOBt, TBTU/HOBt, HATU/HOAt DEPBT/HOOBt, and PyBoP/Cl-HOBt, b) tosylation of the N-α-amino group of the glycine moiety, c) cleavage of the tosylated peptide or of an amino side chain protected derivative thereof from the solid phase support to form the peptide intermediate of formula II

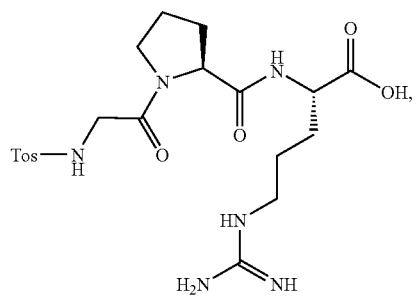

II or an amino side chain protective derivative thereof; and d) reaction, in the presence of a second coupling agent/additive system, of the peptide intermediate of the formula

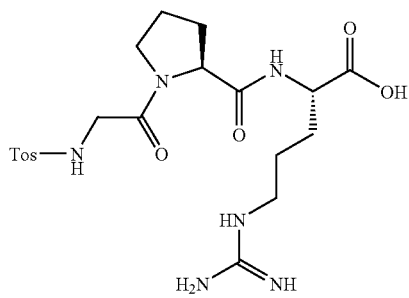

II or of an amino side chain protected derivative thereof with an aniline of the formula

R—$NH_2$ III wherein R has the meaning of p-aminophenyl and wherein one amino group is protected with an amino protecting group, wherein the second coupling agent/additive system for the reaction of the peptide intermediate of formula II with the aniline of formula III is selected from the group consisting of DCC/HOBt, HATU/HOAt, HBTU/HOBt, TBTU/HOBt, PyBOP/Cl-HOBt and DEPBT/HOOBt.

2. The process of claim 1, wherein arginine is side chain protected with a Pbf or a Pmc protecting group.

3. The process according to claim 1, characterized in that proline is applied in the form of Fmoc-(L)-Pro-OH.

4. The process according to claim 1, characterized in that glycine is applied in the form of Fmoc-Gly-OH.

5. The process according to claim 3, wherein the Fmoc protecting group is removed by treatment with piperidine.

6. The process according to claim 4, wherein the Fmoc protecting group is removed by treatment with piperdine.

7. The process according to claim 1, wherein the first coupling agent/additive system is HBTU/HOBt.

8. The process according to claim 1, wherein the second coupling agent/additive system is DEPBT/HOOBt.

9. The process according to claim 1, wherein the tosylation takes place with 4-toluenesulfonylchloride.

10. The process according to claim 1, wherein the cleavage from the solid phase support of step c) is accomplished with trifluoroacetic acid.

11. The process according to claim 1, wherein the reaction with the aniline of formula III in step d) is performed with Tos-Gly-Pro-Arg(Pbf)-OH as the amino side chain protected derivative of the peptide intermediate of formula II.

* * * * *